United States Patent [19]

Blake et al.

[11] Patent Number: 5,674,887

[45] Date of Patent: Oct. 7, 1997

[54] PREVENTION OF BONE RESORPTION

[75] Inventors: David R. Blake, Worcs., United Kingdom; Jill A. Panetta, Zionsville, Ind.; Mone Zaidi, Middlesex, United Kingdom

[73] Assignees: Eli Lilly and Company, Indianapolis, Ind.; London Hospital Medical College; St. George's Hospital Medical School, both of London, United Kingdom

[21] Appl. No.: 392,463

[22] Filed: Feb. 22, 1995

Related U.S. Application Data

[62] Division of Ser. No. 942,687, Sep. 9, 1992, Pat. No. 5,436,258.

[51] Int. Cl.⁶ .................................................. A61K 31/415
[52] U.S. Cl. ........................................ 514/407; 514/406
[58] Field of Search ................................. 514/406, 407

[56] References Cited

U.S. PATENT DOCUMENTS

| 4,346,094 | 8/1982 | Beck et al. ............................. 548/206 |
| 4,495,195 | 1/1985 | Blake et al. ............................ 514/406 |

FOREIGN PATENT DOCUMENTS

| 513379 | 11/1991 | European Pat. Off. . |
| 2130205 | 5/1984 | United Kingdom . |

OTHER PUBLICATIONS

Bax et al., *Biochem. Biophys. Res. Commun.*, 183(3), 1153–1158 (1992).

Chang et al., *Ann. Rhem. Dis.*, 51, 1223–1229 (1992).

Das, *Prostaglandins Leukot Essent Fatty–Acids*, 44(4), 201–210 (1991).

Garrett et al., *J. Clin. Invest.*, 85 632–639 (1990).

Robinson et al., *J. Clin. Invest.*, 56, 1181–1188 (1975).

Key et al., *Bone*, 11(2), 115–119 (1990).

Rathakrishnan et al., *J. Bone Miner. Res.*, 7, 1139–1148 (1992).

Tiku et al., *J. Immunol.*, 145, 690–696 (1990).

Zaidi et al., *J. Bone Miner Res.*, 7 (Suppl):S242 (1992).

Avitabile et al., *Boll. Soc. Ital. Biol. Sper.*, 67(10–11), 931–7 (1991).

Suda, *Kokubyo Gakkai Zasshi*, 58(3), 603–12 (1991).

Fallon et al., *J. Bone Miner Res.*, 1 (Suppl):1 (1986).

Okabe et al., *Bull. Kanagawa Dent. Coo.*, 18(2), 151–9 (1990).

*Primary Examiner*—Jerome D. Goldberg
*Attorney, Agent, or Firm*—Janelle D. Strode; James J. Sales; Kathleen R.S. Page

[57] ABSTRACT

The administration of a xanthine oxidase inhibitor is effective for the treatment or prevention of the excessive resorption of bone in conditions such as osteoporosis and the like.

11 Claims, No Drawings

5,674,887

PREVENTION OF BONE RESORPTION

This application is a division of application Ser. No. 07/942,687, filed Sep. 9, 1992, now U.S. Pat. No. 5,436,158.

FIELD OF THE INVENTION

The present invention belongs to the fields of pharmaceutical chemistry and the pathology of bone, and provides a method of treating and preventing the excessive resorption of bone by treatment of the patient with an inhibitor of xanthine oxidase.

BACKGROUND OF THE INVENTION

A number of dangerous and painful disabilities are caused by the excessive resorption of bone. For example, rheumatoid arthritis and periodontitis (both associated with erosive joint disease), osteoporosis, and the failure of prostheses to remain tightly bonded to the underlying bone are all characterized by the excessive resorption of existing bone. Medical research has studied such conditions for some time, but problems have not yet been resolved and treatment methods remain only partially satisfactory.

The mechanism of bone resorption is still the subject of research and speculation. It is known that a class of cells called osteoclasts have the function of resorbing bone, in balance with the formation of new bone by the osteoblasts. Bone loss occurs when the osteoclasts become more active than normal, compared with the osteoblasts. The mechanism by which the functions of bone formation and resorption are balanced, and, accordingly, the mechanism by which unbalance occurs with resulting excessive resorption of bone, continue to be discussed and studied. It has recently been shown that osteoclasts in cell culture can be stimulated by hydrogen peroxide, a member of the class of reactive oxygen species. Bax et al., *Stimulation of Osteoclastic Bone Resorption by Hydrogen Peroxide*, BBRC, 183, 1153–58 (1992).

There is at present no generally applicable treatment for excessive bone resorption. Estrogens are administered to post-menopausal women for the treatment of osteoporosis, as is well known, but the side effects of such treatment are also well known and the method is not generally applicable to other cases of excessive bone resorption. Thus, medical science is in need of a general treatment for excessive bone resorption, and continues to search for it.

SUMMARY OF THE INVENTION

The present invention provides a method of treating or preventing the excessive resorption of bone comprising the administration of a pharmaceutically acceptable inhibitor of xanthine oxidase to a patient in need of such treatment.

In a more preferred aspect of the invention, the xanthine oxidase inhibitor administered is a compound of the formula

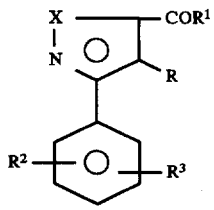

I wherein X is a sulfur atom, a nitrogen atom, or a methyl-substituted nitrogen atom;

R is hydrogen, amino, $C_1$–$C_3$ alkylamino, or hydroxy;

$R^1$ is hydroxy, or OM;

M is a nontoxic cation;

$R^2$ and $R^3$ independently represent hydrogen, halo, $C_1$–$C_3$ alkyl, trifluoromethyl, or $C_1$–$C_3$ alkoxy.

The invention also comprises the use of pharmaceutically acceptable xanthine oxidase inhibitors, particularly the compounds of formula I, for the prevention of excessive bone resorption, and still further provides pharmaceutical compositions adapted for such administration.

DESCRIPTION OF THE PREFERRED EMBODIMENTS

The Compounds

A large number of compounds have been identified as possessing the ability to inhibit the well known enzyme, xanthine oxidase (XO). The treatment of gout, in particular, has been identified with the inhibition of xanthine oxidase for many years, and allopurinol is the best-known XO inhibitor and is used somewhat satisfactorily as a treatment for gout. However, a great number of types of compounds have been shown to be capable of inhibiting XO, and pharmaceutical chemists are well aware of those compounds and manners in which they may be used for such purpose. For example, the following patent documents are easily accessible and disclose groups of XO inhibitors, as follows.

European 429,038, phenylethenyl esters of phenylpropenoic acid;

PCT Publication 9113623, C5-monosubstituted barbiturates;

Czechoslovakia 264505, salts of N-acetyl-p-aminosalicylic acid;

German 3912092, heterocyclic compounds with more than one hetero atom, such as aminotriazolopyridoquinazolinone;

Japanese 02245198, phenol compounds such as sodium salicylate;

European 269859, pyrazolotriazines;

European 274654, heterocylotriazinones such as 7-phenylisothiazolo[4,5-d]-1,2,3-triazin-4(3H)-one;

Netherlands 8602382, catechol derivatives such as 4-(+)-menhylthiocatechol;

German 3632841, similar to the above;

German 3632824, bicyclic catechol derivatives;

Japanese 59219229, indoles, such as 1-formyl-4-hydroxy-9H-pyrido[3,4-b]indole;

U.S. Pat. No. 4,336,257, 2-(4-pyridyl)-5-chlorobenzimidazole, 1H-imidazo[4,5-b]pyridines, and imidazo[4,5-c]pyridines;

European 28660, pyrazolobenzotriazine derivatives;

Japanese 55055185, compounds derived from extraction of picrasma quassioides;

German 2941449, pyridolindoles isolated according to the above patent;

U.S. Pat. No. 4,110,456, imidazoles, including sulfamoylimidazoles;

U.S. Pat. No. 4,021,556, pyrazolopyrimidines, pyrazolopyrimidinols and pyrazolopyrimidinediols;

U.S. Pat. No. 4,032,522, trifluoromethylimidazoles;

U.S. Pat. No. 3,988,324, heterocyclobenzothiadiazinesulfonamides;

Japanese 51054576, hydroxy or acyloxyalkylaminobenzothiadiazines;

U.S. Pat. No. 3,960,854, 7-mercapto (or thio) benzothiadiazine-1,1-dioxides;

U.S. Pat. No. 3,969,518, 3-haloalkyl benzothiadiazine-1,1-dioxides;

U.S. Pat. No. 3,951,966, heterocycle-substituted benzothiodiazines;

Japanese 51006992, dihydrothiazoloadenines;

Japanese 51006993, imidazoadenines and pyrimidinoadenines;

French 2262977, formylaminoallylidenehydrazines, substituted with aryl groups;

French 2262976, formamidrazones, substituted with aryl groups;

German 2410650, formamidrazones, isonicotinyl pyrimidinones and the like;

German 2410579, orotic acid hydrazide, and the corresponding nicotinic and isonicotinic acid derivative;

German 2509130, acryloylformamidrazones, pyrimidinones and the like;

German 2410653, acylpyrazolocarboxamides;

German 2508934, formylcarbamoylpyrazoles substituted with heterocyclic and carbocyclic aryl groups;

German 2410611, nicotinic acid hydrazide, azapentadienylidene;

German 2509094, aminoazapentadienylidene hydrazine;

German 2509049, morpholinoacryloyl-formamidrazones substituted with various aryl groups;

German 2509175, substituted 2-hydrazonomethyl-3-hydroxy-4-aza-2,4-pentadiene-nitriles;

U.S. Pat. No. 3,892,858, 7-alkylsulfonyl-substituted-benzothiadiazine 1,1-dioxides;

German 2410614, heterocyclic N-acyl-N'-3-amino-2-cyanoacryloyl) formamidrazones;

U.S. Pat. No. 3,907,799, imidazopyrimidinediols;

Japanese 50004039, salicylanilides;

British 1403974, dioxo-6,6-azopurine;

Japanese 49072298, 9-substituted palmatine derivatives;

German 2457127, haloimidazoles substituted with pyridyl and the like;

Japanese 49127943, 4-(2-hydroxybenzamido)-salicylic acids;

German 2418467, hydroxybenzanilides;

Japanese 49048664, hydroxyalkyl imidazoles;

U.S. Pat. No. 3,816,625, 7-alkylsulfonyl-substituted benzothiadiazine-1,1-dioxides;

U.S. Pat. No. 3,816,626, 3-pyridyl-1,2,4-benzothiadiazine-1,1-dioxides;

U.S. Pat. No. 3,816,631, 6-sulfamoyl-7-substituted-(3H) quinazolinones;

German 2356690, pyrazolo[3,4-d]pyrimidine N-oxides;

German 2344757, 2-cyanopyrimidine-4(1H)ones;

German 2351126, 6-sulfamoyl-4(3H)-quinazolinones;

German 2343702, 4-mercapto-1H-pyrazolo[3,4-d]pyrimidine;

German 2344733, 3-chloro-2-(hydrazonomethyl)-4-aza-2,4-pentadienenitriles;

German 2344738, 2-hydrazonomethyl-3-hydroxy--aza-2,4-pentadienenitriles;

German 2224379, 7-βD-ribofuranosyl-4,6-dihydroxypyrazolo[3,4-d]pyrimidine;

German 2318784, N-(2,4-dihydroxybenzoyl)-4-aminosalicylic acids;

Japanese 48067491, formyluracils;

German 2313573, 7-mercapto-1,2,4-benzothiadiazine 1,1-dioxide;

German 2313636, benzothiadiazines substituted with heterocyclic groups;

German 1966640, 4-hydroxypyrazolo[3,4-d]pyrimidines;

French 2143577, 3-(2-chlorobenzoylamino)-benzoic acid derivatives;

German 2255247, 5-(5-indanyloxy)tetrazoles;

German 2236987, pyrazolo[1,5-a]pyrimidines;

French 2109005, 4-(2-quinoxalinyl)-phenoxyacetic acid derivatives;

French 2081360, 2,5-disubstituted imidazoles;

German 2147794, 1,2,4-triazoles substituted with heterocyclic and other aryl groups;

German 1814082, allopurinol and oxypurinol;

German 1927136, 1-D-ribosylallopurinol;

French 4777, 4-mercaptopyrazolo[3,4-d]pyrimidine;

French 1480652, 4-oxo-5-alkylpyrazolo[3,4-d] pyrimidines.

It will be understood by the pharmaceutical chemist to whom this document is addressed that xanthine oxidase inhibitors are numerous, and that the present invention may be carried out with any of the class of pharmaceutically acceptable xanthine oxidase inhibitors.

A particularly preferred class of xanthine oxidase inhibitors is comprised of the compounds of formula I, as shown above. These compounds were disclosed by Beck et al. in U.S. Pat. Nos. 4,346,094, 4,495,195 and 4,544,752, all of which are incorporated by reference herein. The nature and synthesis of the compounds are well taught in those patents, and so only a brief discussion is necessary here.

In formula I, the group X can be a sulfur atom, a nitrogen atom or a methyl-substituted nitrogen atom. Thus, since the isothiazole and pyrazole rings are both aryl, that is, fully unsaturated, the location of the double bonds in those rings depends on the nature of the X group, as will be readily understood by the reader. The various possible configurations of that ring are well explained and exemplified in the three Beck et al. patents.

The carboxylic acid group on the pyrazole or isothiazole ring may exist as the acid itself, or as a salt, in which the cation of the salt is represented by M. Pharmaceutical chemists often prepare such drugs as alkali metal salts, wherein M would be sodium, potassium or lithium. M can also be alkaline earth cations such as magnesium or calcium, a nontoxic metal cation such as aluminum or zinc, or an ammonium ion such as piperazinium, butyltrimethylammonium, piperidinium, phenyl-triethylammonium and the like.

The preferred salt-forming moieties, M, include alkali metals and quaternary ammonium groups. More particularly, sodium, potassium, lithium, and quaternary ammonium groups wherein the nitrogen atom is substituted with four hydrogen, $C_1$–$C_{18}$ alkyl, phenyl or benzyl moieties are preferred.

For example, quaternary ammonium groups such as ammonium, tetramethylammonium, diethyl-dimethylammonium, diethyl-dibutylammonium, benzyltrimethylammonium, t-butyl-trimethylammonium, phenyl-triethylammonium, diethyldipropylammonium, s-butyl-trimethylammonium, isobutyltriethylammonium, dimethyl-bis(tetradecyl)ammonium, trimethyl-octadecylammonium, diethyl-decyl-heptadecylammonium and the like are useful and may be chosen for convenience in the circumstances.

A few members of the class of compounds used in this invention will be specifically mentioned, to assure the reader's comprehension.

1-methyl-3-phenyl-4-aminopyrazole-5-carboxylic acid, sodium salt 1-methyl-3-(4-fluorophenyl)-4-aminopyrazole-5-carboxylic acid 1-methyl-3-(3-iodophenyl)pyrazole-5-carboxylic acid, calcium salt 1-methyl-3-(4-methylphenyl)-4-ethylamino-pyrazole-5-carboxylic acid, ammonium salt 1-methyl-3-(3-ethylphenyl)-4-hydroxypyrazole-5-carboxylic acid, potassium salt 3-phenyl-4-hydroxypyrazole-5-carboxylic acid, magnesium salt 1-methyl-3-(3-methoxyphenyl)pyrazole-5-carboxylic acid, tetramethylammonium salt 3-(3,4-dimethoxyphenyl)-4-aminopyrazole-5-carboxylic acid, aluminum salt 3-(3-chloro-4-methylphenyl)-pyrazole-5-carboxylic acid, lithium salt 1-methyl-3-(3,4-difluorophenyl)-4-aminopyrazole-5-carboxylic acid 3-(4-trifluoromethyl-3-fluorophenyl)-4-hydroxypyrazole-5-carboxylic acid 3-(4-ethylphenyl)-4-aminopyrazole-5-carboxylic acid, tetraethylammonium salt 3-(4-trifluoromethylphenyl)pyrazole-5-carboxylic acid 1-methyl-3-(3-trifluoromethylphenyl)-pyrazole-5-carboxylic acid 1-methyl-3-(3-trifluoromethylphenyl)-4-propylaminopyrazole-5-carboxylic acid, sodium salt 3-(3-trifluoromethylphenyl)-4-hydroxypyrazole-5-carboxylic acid, ammonium salt 1-methyl-3-(3-trifluoromethylphenyl)-4-aminopyrazole-5-carboxylic acid, potassium salt 3-(3-trifluoromethylphenyl)-4-aminopyrazole-carboxylic acid, calcium salt 3-(3-trifluoromethyl-4-chlorophenyl)-4-hydroxypyrazole-5-carboxylic acid 1-methyl-3-(3-trifluoromethyl-5-methoxyphenyl)-4-hydroxypyrazole-5-carboxylic acid, zinc salt 3-(4-fluorophenyl)-4-hydroxyisothiazole-5-carboxylic acid 3-(3-chlorophenyl)isothiazole-5-carboxylic acid, calcium salt 3-(4-methylphenyl)-4-methylamino isothiazole-5-carboxylic acid, ammonium salt 3-(3-ethylphenyl)-4-hydroxyisothiazole-5-carboxylic acid, potassium salt 3-(3-methoxyphenyl)-4-methylamino-isothiazole-5-carboxylic acid 3-(3,4-dimethoxyphenyl)-4-propylamino-isothiazole-5-carboxylic acid, aluminum salt 3-(3-chloro-4-methylphenyl)isothiazole-5-carboxylic acid, magnesium salt 3-(3,4-difluorophenyl)-4-aminoisothiazole-5-carboxylic acid 3-(4-trifluoromethyl-3-bromophenyl)-4-hydroxyisothiazole-5-carboxylic acid 3-(4-ethylphenyl)-4-aminoisothiazole-5-carboxylic acid, tetraethyl ammonium salt 3-(4-trifluoromethylphenyl)isothiazole-5-carboxylic acid 3-(3-trifluoromethylphenyl)isothiazole-5-carboxylic acid 3-( 3- trifluoromethylphenyl )- 4-hydroxyisothiazole-5-carboxylic acid, sodium salt 3-(3-trifluoromethylphenyl)-4-ethylamino-isothiazole-5-carboxylic acid, ammonium salt 3-(3-trifluoromethylphenyl)-4-aminoisothiazole-5-carboxylic acid, potassium salt 3-(4-trifluoromethylphenyl )-4-aminoisothiazole-5-carboxylic acid, calcium salt 3-(3-trifluoromethylphenyl-5-ethylphenyl)-4-aminoisothiazole-5-carboxylic acid 3-( 3-trifluoromethylphenyl)-4-hydroxyisothiazole-5-carboxylic acid, magnesium salt 3-( 3-trifluoromethyl-4-methoxyphenyl)-4-hydroxyisothiazole-5-carboxylic acid, zinc salt A number of subgroups of the compounds of formula I are particularly preferred for use in the present invention. The following paragraphs list a number of such preferred categories of compounds; it will be understood that the various individual limitations listed below can be combined to create further, more narrowly limited groups of compounds.

a) X is a sulfur atom;
b) X is a nitrogen atom;
c) X is a methyl-substituted nitrogen atom;
d) R is hydrogen or amino;
e) R is amino or alkylamino;
f) R is hydroxy or hydrogen;
g) $R^1$ is hydroxy;
h) $R^1$ is OM;
i) M is a metal ion;
j) M is an ammonium ion;
k) one and only one of $R^2$ and $R^3$ is hydrogen;
l) $R^2$ and $R^3$ independently represent hydrogen, halo or trifluoromethyl;
m) $R^2$ is hydrogen and $R^3$ is trifluoromethyl;
n) $R^2$ and $R^3$ independently represent hydrogen, alkyl or alkoxy.

The methods of synthesis of the compounds used in the present invention are taught by Beck et al. in the above-mentioned patents, to which the skilled reader can easily refer.

The Patient and the Disease

A very wide variety of diseases and conditions result in excessive bone resorption, which can be both treated and prevented by use of the present method. Risk factors which create an increased possibility of excessive bone resorption are known, and include advanced age, being of Caucasian origin and small stature, being of asthenic build, and being female, particularly post-menopausal and if nulliparous. People of advanced age, of either sex, are also well known increased risks. A number of exogenous events also create increased risk of bone resorption: alcohol abuse, a low calcium diet, a low degree of physical activity, smoking, continued use of aluminum antacids, and steroid use or abuse all militate toward increased bone resorption.

Osteoporosis, of course, is the classic disease manifested by excessive bone resorption. The present method can be used in all of the types of osteoporosis, including post-menopausal, senile and idiopathic osteoporosis. It is equally useful in Paget's bone disease, rheumatoid arthritis, periodontal bone disease and alcoholic bone disease. Further, the method may be used to prevent and treat excessive bone resorption caused by malignancies, including bone metastasis from any type of cancers, hypercalcaemia of malignancy, lymphoma, leukemia, multiple myeloma, and excessive resorption caused by Waldenstrom's macroglobulinemia.

Further, the method may be applied against excessive bone resorption resulting from endocrine and endocrine-related disorders, such as primary hyperperithyroidism, hypogonadism, Cushing's syndrome, thyrotoxicosis, and diabetes mellitus. Still further, diseases and conditions of the kidneys can result in excessive bone resorption. The present method can be used to prevent and treat such increased bone resorption caused by, for example, renal osteodystrophy, including secondary hyperperithyroidism, renal tubular acidosis, nephrotic syndrome, and Fanconi's syndrome, of both the primary and secondary types. Conditions corresponding to secondary Fanconi's syndrome include, for example, cystinosis, glycogenosis, Low's syndrome, Wilson's disease, tyrosinemia, neurofibromitosis, kidney transplants, and toxicities caused by, for example, cadmium, lead and tetracycline drugs. It is also known that gastrointestinal disorders can result in excessive bone resorption. Such disorders include Crohn's disease, ulcerative colitis, intestinal diverticulitis, and malabsorption syndrome, such as lactose intolerance, steatorrhea, prolonged obstructive jaundice, and malabsorption following surgery, such as partial gastrectomy.

The hereditary conditions Down's syndrome and Riley Day syndrome can also result in excessive bone resorption. Further, iatrogenic causes, such as chronic heparin treatment, methotrexate treatment, and hemodialysis can at times result in excessive bone resorption.

Still other conditions are known to result in excessive bone resorption in some cases. For example, epilepsy, chronic obstructive pulmonary disease, Menke's syndrome, adult hypophosphatasia, systemic mastocytosis, ankylosing spondylitis, metabolic acidosis, cystic fibrosis, scurvy and any condition which results in prolonged immobilization of the patient, may do so.

Still further, additional conditions and diseases which frequently result in excessive bone resorption include, for example, milk intolerance, prosthesis loosening, anorexia nervosa, Type I diabetes, occult osteogenesis imperfecta, prolonged parenteral nutrition, prolactinoma, transient osteoporosis, henolytic anemia, and other forms of anemia, lipidoses, Ehlers Danlos syndrome, Marfan's syndrome, homocystinurina, pregnancy and lactation, chronic hypophosphatemia, hyperphosphatasia, and continued administration of a number of drugs and therapies, including, for example, anticoagulants, thyroid replacement therapy, lithium therapy, chemotherapy of breast cancer or lymphoma, gonadatrophin agonist therapy, anticonvulsants, diuretics which produce calciuria, phenothiazines, cyclosporin A, and the chronic use of phosphate binding antacids.

The method of the present invention can be used beneficially both to treat patients suffering from excessive bone resorption caused by any of the above-described conditions and diseases, as well as others, and to prevent the onset of excessive bone resorption in patients who are at risk thereof. The preferred use of the present invention is to prevent and treat excessive bone resorption associated with rheumatoid arthritis, osteoporosis, prosthesis loosening, periodontal diseases, tumors or Paget's disease. In the practice of the present invention, it will be found that excessive bone resorption can be reversed, with the result that bone is redeposited and the original strength of bone is approached, when patients suffering from excessive bone resorption are treated appropriately with the presently-described treatment agents.

Methods of Administration

It will be understood that the present method of treatment may be applied to patients prophylactically when such patients have an underlying condition which demonstrates that the patient is in danger of excessive bone resorption, and is therefore in need of such prophylactic treatment. Prophylactic treatment may be continued for long periods of time safely, or may be applied to a patient for a brief period of time when the onset of excessive bone resorption is for any reason believed to be probable. Any of the compounds described above may be used prophylactically, but the compounds of formula I are preferred for such purpose, as has been discussed.

Whenever a patient is in a condition of excessive bone resorption, the treatment method of the present invention may and should be applied to treat the condition, reducing or even eliminating the increased rate of excessive bone resorption, and allowing the rebuilding of bone which has been weakened or lost through such resorption. Such treatment may be continued for as long as the condition persists, or may be applied only briefly during a period of acute resorption, and may be continued in a prophylactic mode when the condition of excessive resorption has been arrested. The dose of xanthine oxidase inhibitor according to the present invention will, of course, be fixed by the attending physician, in the general range of from about 0.1 to about 100 mg/kg/day. Administration of the dosage in divided doses is often beneficial. Choice of a dose of a drug from the preferred range of from about 0.5 to about 50 mg/kg/day is often beneficial, and a more preferred range of dosages is from about 0.1 to about 10 mg/kg/day.

The xanthine oxidase inhibitors used in the present invention may be administered by any route which makes the particular compound available in the body. In general, it is preferable in all cases to administer drugs orally, for convenience of the patient. The usual oral dosage forms, such as tablets, capsules, suspensions and the like, may be prepared according to the usual pharmaceutical methods, and conveniently used. Other routes of administration, including rectal, intravenous, intramuscular and the like may be used if the particular compound is not adequately orally absorbed, or if a particular group of patients prefers such administration. It is frequently economical and convenient to prepare an injectable depot formulation, so that a single injection will be effective for a prolonged period of time, and such administration is often preferred for a long-continued treatment of a condition such as excessive bone resorption, where treatment may well be prolonged for months or years.

If a depot formulation is not used, the frequency of administering the xanthine oxidase inhibitor must be carefully considered, in order to maintain an adequate concentration of the compound in the body as a whole, and in the tissue, bone, where the mechanism of bone resorption takes place.

The site of effect of the present method is, of course, those areas of bone where excessive resorption is occurring, frequently in joints. A method of administration which tended to concentrate the xanthine oxidase inhibitor at such sites, rather than dispersing it evenly throughout the body, would clearly be advantageous. Methods for targeting drugs and other treatment agents by use of antibodies, for example, are now in use and such methods are desirable for the administration of the present xanthine oxidase inhibitors for use in this invention.

In the following example, the relatively new technique of measuring surface plasmon resonance was used. The technique is now well known in the literature; see, for example, Fagerstam et al., Detection of antigen-antibody interactions by surface plasmon resonance, *J. Mol. Recognition*, 3,208–14 (1990); Karlsson et al., Kinetic analysis of monoclonal antibody-antigen interactions with a new biosensor based analytical system, *J. Immunol. Methods*, 145, 229–40 (1991); Jonsson et al., Real-time biospecific interaction analysis using surface plasmon resonance and a sensor chip technology, *BioTechniques*, 12, 620–7 (1991); and Lofas et al., A novel hydrogel matrix on gold surfaces in surface plasmon resonance sensors for fast and efficient covalent immobilization of ligands, *J. Chem Soc. Chem. Commun.*, 21 (1990). The technique is carried out by measuring changes in refractive index close to a metal, usually gold in this case, surface. As the above articles, and many others, explain, the technique is very useful for the determination of interactions between biomolecules, such as antigens and antibodies, and is conveniently used in the present instance to demonstrate the binding of xanthine oxidase by purified monoclonal antibodies. The source of the BIACore instrument used in the technique and the chips and other materials was Pharmacia, of Uppsala, Sweden.

The Presence of Xanthine Oxidase

Tests were carried out to demonstrate the presence of xanthine oxidase in cultured osteoblasts of the UMR 106.01 cell line (ATCC designation CRL 1661; ECACC designation NO. 90111314). In one test, two monoclonal antibodies, B5 and H3, raised and characterized by Dr. R. Harrison, University of Bath Bath, England, were used to bind three commercially available xanthine oxidase preparations, and lysates from the rat osteoblast cultures. These antibodies were raised against purified bovine and human xanthine oxidase, respectively. The tests were carried out by attaching antibody to sensor-chip CM5 (Pharmacia) by first coating rabbit anti-mouse immunoglobulin (from Dakopatts Ltd) on the sensor-chip, and then capturing the antibody on the immunoglobulin. Then the sensor-chip was exposed to xanthine oxidase (obtained from Calbiochem, Biozyme or Sigma in different tests) or against the osteoblast lysate, and the real-time binding interaction was assessed by the surface plasmon resonance measurements.

It was found that xanthine oxidase from all three sources bound specifically to both of the antibodies, and that similar results were obtained when the enzymes were replaced with osteoblast lysates, providing evidence that the enzyme is present in the osteoblast cell line.

EXAMPLE

Rat osteoclasts were obtained by curetting the long bones of two neonatal rats into 2 ml Medium 199 (buffered with HEPES and supplemented with 10% foetal calf serum [FCS]) and agitating the suspension with a pipette. The supernatant was pipetted onto 30 to 36 bone slices previously placed in a Cel-Cult (Serilin) 20 mm×20 mm well. Following incubation at 37° C. for 30 minutes the bone slices were gently removed, rinsed in minimal essential medium (MEM) (buffered with 0.85 g/l sodium bicarbonate and supplemented with 100 µg/ml streptomycin and 100 IU/ml penicillin), placed in a second Cel-Cult well containing 1 ml Medium 199 (buffered with 2.2 g/l sodium bicarbonate and supplemented with 10% FCS, penicillin, streptomycin and glutamine) and incubated at 37° C. in a humidified 10% carbon dioxide atmosphere. Meanwhile UMR 106.01 cells were trypsinized, washed twice and suspended in Medium 199 (buffered with 2.2 g/l sodium bicarbonate and supplemented with 10% FCS, penicillin, streptomycin and glutamine) at a density of $1\times10^6$ cells/ml. One ml of the cell suspension was gently pipetted onto the bone slices with attached osteoclasts and were left undisturbed for 4 hours in a humidified 10% carbon dioxide atmosphere, at a temperature of 37° C. The bone slices were then removed, washed in MEM (buffered with 0.85 g/l sodium bicarbonate) and placed in separate wells (each well containing bone slices) with 2 ml MEM (0.85 g/l sodium bicarbonate and supplemented with penicillin, streptomycin and glutamine) containing the appropriate test substance (1 nmol/l tumour necrosis factor, 1 µmol/l 3-(3-trifluoromethyl)-4-aminoisothiazole-5-carboxylic acid, both, or vehicle). The co-cultures were maintained for 18 hours at 37° C. in a humidified carbon dioxide atmosphere. After incubation, the bone slices were removed from the Cel-Cult wells and immersed in 10% NaOCl for 10 minutes to remove cells. Following three washes in distilled water, dehydration in ethanol and air drying, the bone slices were mounted on an aluminum stub and sputter coated with gold.

Tumor necrosis factor is used in the test because, as a cytokine, it both regulates osteoclast formation directly, and also influences osteoclast function indirectly, via the osteoblast. See, for example, Vaes, *Clinical Orthopedics*, 231, 239–71 (1988) and Roodman, *Critical Reviews in Oral Biology and Medicine*, 2, 289–409 (1991).

Bone resorption was assessed by scanning electron microscopy; the outlines of the excavations were traced onto acetate sheets. The excavation areas (arbitrary units) were assessed using a hand scanner linked to an IBM computer. Control cultures resorbed at the rate of 687 units. Addition of the isothiazole compound reduced the rate to 560 units, showing marginal inhibition. When the tumor necrosis factor was added to the control cultures, however, the rate drastically increased to 1689 units, illustrating excessive bone resorption. Addition of the isothiazole compound to the stimulated, excessively resorptive cultures reduced the resorption rate down to 741 units, close to the control rate, illustrating the ability of the present treatment method to treat excessive bone resorption.

EXAMPLE

The activity of a xanthine oxidase inhibitor in reducing the resorption of bone was assessed in a model wherein osteoblast cells of the UMR 106.01 cell line were grown on microcarrier beads and the presence of oxidizing species was determined.

UMR 106.01 cells were grown on Cytodex 3 microcarrier beads (Pharmacia), and, when they had grown to confluence, were washed twice in Dulbecco A phosphate buffered saline (PBS) and allowed to sediment as aliquots of packed beads and cells. A 150 µl sample of packed beads was added to 50 µl of 10 mM 3,5-dibromo-4-nitrosobenzenesulfonate (DBNBS) and 50 µl of PBS. Other aliquots of the same size were treated by the addition of $10^{-8}$M 3-(3-trifluoromethylphenyl)-4-aminoisothiazole-5-carboxylic acid, a xanthine oxidase inhibitor of formula I.

The aliquots of cells were then incubated at 37° C. for periods of time, after which small samples of the mixture were analyzed for the presence of oxidized DBNBS by electron spin resonance spectrometry, using a JEOL RE1X ESR spectrometer (JEOL). DBNBS is known to be a useful spin trap in such analyses and shown to produce a characteristic 3-line spectrum in contact with oxidizing species. Yang et al., Free radical yields from the homolysis of peroxynitrous acid, *Free Rad. Biol. Med.*, 12, 327-30 (1992).

The most conspicuous effect of the isothiazole compound was observed after 40 minutes of incubation, at which time a reduction in the oxidation of DBNBS of more than 50% was observed, compared to the same reaction without the isothiazole compound.

We claim:

1. A method of treating or preventing the excessive resorption of bone comprising the administration of an effective amount of a pharmaceutically acceptable inhibitor of xanthine oxidase sensitive to bone disorders to a patient in need of said treatment.

2. A method of claim 1 wherein the excessive resorption of bone is associated with osteoporosis or periodontal diseases.

3. A method of claim 1 wherein the excessive resorption of bone is associated with prosthesis loosening or tumors.

4. A method of claim 1 wherein the excessive resorption of bone is associated with rheumatoid arthritis or Paget's disease.

5. A method of claim 1 wherein the inhibitor of xanthine oxidase is a compound of the formula

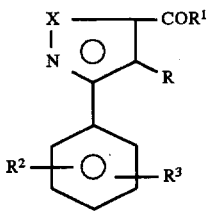

wherein X is a nitrogen atom, or a methyl-substituted nitrogen atom;

R is hydrogen, amino, $C_1$–$C_3$ alkylamino, or hydroxy;

$R^1$ is hydroxy, or OM;

M is a nontoxic cation;

$R^2$ and $R^3$ independently represent hydrogen, halo, $C_1$–$C_3$ alkyl, trifluoromethyl, or $C_1$–$C_3$ alkoxy.

6. A method of claim 5 wherein the excessive resorption of bone is associated with osteoporosis or periodontal diseases.

7. A method of claim 5 wherein the excessive resorption of bone is associated with prosthesis loosening or tumors.

8. A method of claim 5 wherein the excessive resorption of bone is associated with rheumatoid arthritis or periodontal diseases.

9. A method of claim 5 wherein the inhibitor of xanthine oxidase is a compound wherein $R^2$ and $R^3$ independently represent hydrogen, halo or trifluoromethyl.

10. A method of claim 5 wherein the inhibitor of xanthine oxidase is a compound wherein R is hydrogen or amino.

11. A method of claim 10 wherein the excessive resorption of bone is associated with osteoporosis, prosthesis loosening, rheumatoid arthritis, periodontal diseases, tumors or Paget's disease.

* * * * *